US011026764B2

(12) United States Patent
Kopp

(10) Patent No.: US 11,026,764 B2
(45) Date of Patent: Jun. 8, 2021

(54) CANNULA ASSEMBLIES FOR USE WITH ROBOTIC SURGICAL SYSTEMS

(71) Applicant: Covidien LP, Mansfield, MA (US)

(72) Inventor: Brock Kopp, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 387 days.

(21) Appl. No.: 16/304,553

(22) PCT Filed: May 24, 2017

(86) PCT No.: PCT/US2017/034178
§ 371 (c)(1),
(2) Date: Nov. 26, 2018

(87) PCT Pub. No.: WO2017/205467
PCT Pub. Date: Nov. 30, 2017

(65) Prior Publication Data
US 2019/0290389 A1    Sep. 26, 2019

Related U.S. Application Data

(60) Provisional application No. 62/341,888, filed on May 26, 2016.

(51) Int. Cl.
*A61B 90/50* (2016.01)
*A61B 34/30* (2016.01)
*A61B 17/34* (2006.01)

(52) U.S. Cl.
CPC .......... *A61B 90/50* (2016.02); *A61B 17/3421* (2013.01); *A61B 17/3462* (2013.01);
(Continued)

(58) Field of Classification Search
CPC ..... A61B 90/50; A61B 34/30; A61B 17/3462; A61B 17/3421; A61B 2034/302; A61B 2017/3419
See application file for complete search history.

(56) References Cited

U.S. PATENT DOCUMENTS 4,950,257 A * 8/1990 Hibbs ............... A61M 25/0069
604/167.02
5,127,626 A * 7/1992 Hilal .................. A61B 17/3462
251/149.1
(Continued)

FOREIGN PATENT DOCUMENTS

| EP | 1625863 A2 | 2/2006 |
|---|---|---|
| WO | 2015088647 A1 | 6/2015 |
| WO | 2018027788 A1 | 2/2018 |

OTHER PUBLICATIONS

International Search Report and Written Opinion corresponding to counterpart Int'l Appln. No. PCT/US2017/034178 dated Sep. 12, 2017.
(Continued)

*Primary Examiner* — Phong Son H Dang

(57) ABSTRACT

The present disclosure relates to cannula assemblies for use with robotic surgical systems. According to an aspect of the present disclosure, a surgical cannula assembly for use with a mounting structure of a robotic arm, is provided. The surgical cannula assembly includes a cannula configured for reception of a surgical instrument at least partially therethrough; an attachment mechanism configured to releasably engage the cannula; and a barrier configured to extend through a channel of the mounting structure. The barrier includes a proximal ring for positioning adjacent a proximal face of the mounting structure, a distal ring for positioning adjacent a distal face of the mounting structure, and a cylindrical section defining a lumen therein and extending between the proximal ring and the distal ring, the cannula configured for insertion within the lumen in a distal-to-proximal direction.

7 Claims, 4 Drawing Sheets

(52) U.S. Cl.
CPC ...... *A61B 34/30* (2016.02); *A61B 2017/3419* (2013.01); *A61B 2034/302* (2016.02)

(56) References Cited

U.S. PATENT DOCUMENTS

| | | | | |
|---|---|---|---|---|
| 5,197,955 | A * | 3/1993 | Stephens | A61M 39/06 604/167.01 |
| 5,354,280 | A * | 10/1994 | Haber | A61B 17/34 604/167.03 |
| 5,458,640 | A * | 10/1995 | Gerrone | A61B 17/3417 604/158 |
| 5,820,600 | A * | 10/1998 | Carlson | A61B 17/3462 604/167.03 |
| 6,702,787 | B2 | 3/2004 | Racenet et al. | |
| 7,144,386 | B2 * | 12/2006 | Korkor | A61M 25/0662 604/164.03 |
| 7,470,255 | B2 * | 12/2008 | Stearns | A61B 17/3421 604/167.01 |
| D606,193 | S * | 12/2009 | Oberlaender | D24/146 |
| 7,744,569 | B2 * | 6/2010 | Smith | A61B 17/3462 604/167.01 |
| 8,002,750 | B2 * | 8/2011 | Smith | A61B 17/3462 604/167.03 |
| 8,715,250 | B2 * | 5/2014 | Tremblay | A61M 5/321 604/263 |
| 8,828,023 | B2 | 9/2014 | Neff et al. | |
| 9,352,118 | B2 * | 5/2016 | Rowe | A61M 39/06 |
| 10,130,431 | B2 | 11/2018 | Lohmeier et al. | |
| 10,265,095 | B2 * | 4/2019 | Franer | A61B 17/3439 |
| 10,463,395 | B2 * | 11/2019 | Reid | A61B 17/3462 |
| 2002/0128604 | A1 * | 9/2002 | Nakajima | A61M 39/0693 604/164.01 |
| 2004/0102738 | A1 * | 5/2004 | Dikeman | A61M 39/24 604/256 |
| 2005/0059934 | A1 * | 3/2005 | Wenchell | A61B 17/3439 604/167.01 |
| 2005/0212221 | A1 * | 9/2005 | Smith | A61B 17/3462 277/628 |
| 2006/0161136 | A1 * | 7/2006 | Anderson | A61B 90/57 606/1 |
| 2008/0065011 | A1 * | 3/2008 | Marchand | A61M 25/0662 604/103.02 |
| 2010/0036323 | A1 * | 2/2010 | Smith | A61B 17/3498 604/167.01 |
| 2010/0274193 | A1 * | 10/2010 | Patton | A61B 17/3462 604/167.01 |
| 2010/0298775 | A1 * | 11/2010 | Berry | A61B 17/3498 604/167.03 |
| 2013/0164075 | A1 | 6/2013 | Murphy | |
| 2013/0218082 | A1 * | 8/2013 | Hyer | A61M 25/0097 604/167.06 |
| 2013/0338679 | A1 | 12/2013 | Rosielle et al. | |
| 2014/0051921 | A1 * | 2/2014 | Miller | A61B 1/00011 600/103 |
| 2014/0166023 | A1 * | 6/2014 | Kishi | G06F 3/01 128/849 |
| 2014/0296872 | A1 | 10/2014 | Cooper et al. | |
| 2015/0105800 | A1 | 4/2015 | Lohmeier et al. | |
| 2018/0008277 | A1 | 1/2018 | Baril | |
| 2018/0042686 | A1 * | 2/2018 | Peine | A61B 34/30 |
| 2019/0000482 | A1 | 1/2019 | Hu et al. | |
| 2019/0053806 | A1 | 2/2019 | Zhang et al. | |
| 2019/0105155 | A1 * | 4/2019 | Gray | A61F 2/962 |

OTHER PUBLICATIONS

Extended European Search Report dated Dec. 10, 2019 corresponding to counterpart Patent Application EP 19191226.0.
Extended European Search Report dated Dec. 19, 2019 corresponding to counterpart Patent Application EP 17803488.0.
Chinese First Office Action dated Oct. 29, 2020 corresponding to counterpart Patent Application CN 201780032025.1.

* cited by examiner

CANNULA ASSEMBLIES FOR USE WITH ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2017/034178, filed May 24, 2017, which claims the benefit of and priority to U.S. Provisional Patent Application Ser. No. 62/341,888, filed May 26, 2016, the entire disclosure of which is incorporated by reference herein.

BACKGROUND

Robotic surgical systems have been used in minimally invasive medical procedures. Some robotic surgical systems include a console supporting a robot arm, and at least one elongated surgical instrument including an end effector such as a forceps or a grasping tool that is mounted to the robot arm via a wrist assembly. During a medical procedure, part of the elongated surgical instrument (e.g., the end effector) is typically inserted into a small incision (via a cannula assembly) or a natural orifice of a patient to position the end effector at a work site within the body of the patient. Moreover, robotic surgical systems may include a first robot arm and mounting structure for supporting an elongated surgical instrument, and at least a second robot arm and mounting structure for supporting a cannula assembly.

Cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the mounting structure and/or the end effector.

It is often desired to re-use parts of the robotic system. As such, it may be important to ensure the sterility of such re-usable components of the robotic system. Accordingly, there is a need to provide a sterile barrier between a cannula of the cannula assembly and the mounting structure associated therewith. It may also be desirable to have the ability to load the cannula into the associated mounting structure in a distal-to-proximal direction to avoid awkwardly lifting the cannula and loading it proximally-to-distally through the mounting structure.

SUMMARY

The present disclosure relates to cannula assemblies for use with robotic surgical systems. According to an aspect of the present disclosure, a surgical cannula assembly for use with a mounting structure of a robotic arm, is provided. The surgical cannula assembly includes a cannula configured for reception of a surgical instrument at least partially therethrough; an attachment mechanism configured to releasably engage the cannula; and a barrier configured to extend through a channel of the mounting structure. The barrier includes a proximal ring for positioning adjacent a proximal face of the mounting structure, a distal ring for positioning adjacent a distal face of the mounting structure, and a cylindrical section defining a lumen therein and extending between the proximal ring and the distal ring, the cannula configured for insertion within the lumen in a distal-to-proximal direction.

The barrier may be configured to provide a sterile barrier between the cannula and the mounting structure during use.

The surgical cannula assembly may further include a first seal disposed within the lumen of the barrier and being configured to provide an air-tight seal about a surgical instrument that is inserted through a hole defined by the first seal.

The surgical cannula assembly may further include a second seal disposed within the lumen of the barrier and being configured to provide an air-tight seal within the lumen of the barrier in the absence of a surgical instrument within the lumen of the barrier.

The first seal and the second seal may be made from the same material as the barrier.

The cannula may be configured for removal from the lumen of the barrier in a proximal-to-distal direction.

The cannula may be configured for removal from the lumen in a distal-to-proximal direction.

According to a further aspect of the present disclosure, a method of engaging a cannula with a mounting structure of a robotic arm is provided. The method includes inserting a portion of a cannula within a channel of the mounting structure in a distal-to-proximal direction, the cannula providing a path through which a surgical instrument can be inserted in a proximal-to-distal direction at least partially therethrough to access a patient.

The method may further include removing the cannula from engagement with the mounting structure in a proximal-to-distal direction.

The method may also include inserting a barrier at least partially within the channel of the mounting structure.

The method may further include engaging an attachment member with the barrier, and removably securing the attachment member to the cannula.

The method may also include removing the cannula from engagement with the mounting structure in a distal-to-proximal direction.

BRIEF DESCRIPTION OF THE DRAWINGS

Embodiments of the present disclosure are described herein with reference to the accompanying drawings, wherein.

DETAILED DESCRIPTION

Figure 1B:
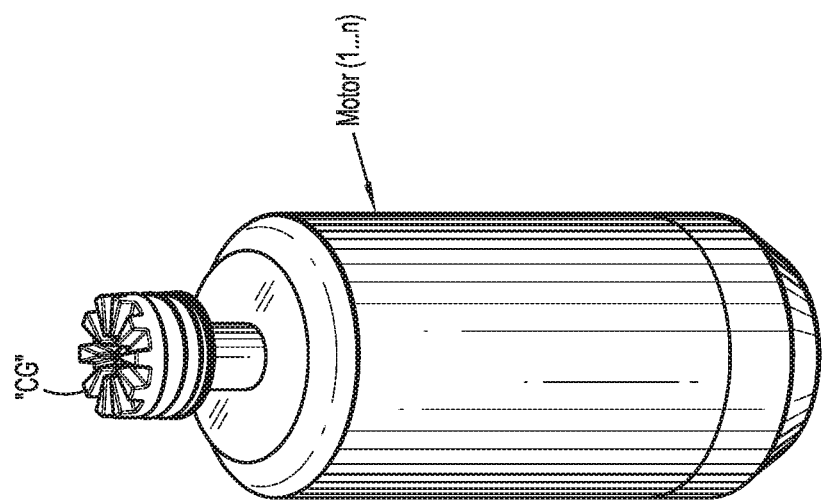
FIG. 1B is a schematic, perspective view of a motor of a control device of the medical work station of FIG. 1A.

Embodiments of the presently disclosed robotic surgical systems and cannula assemblies are described in detail with reference to the drawings, in which like reference numerals designate identical or corresponding elements in each of the several views. As used herein the term "distal" refers to that portion of the system or assembly that is farther from the user, while the term "proximal" refers to that portion of the system or assembly that is closer to the user.

Figure 1A:
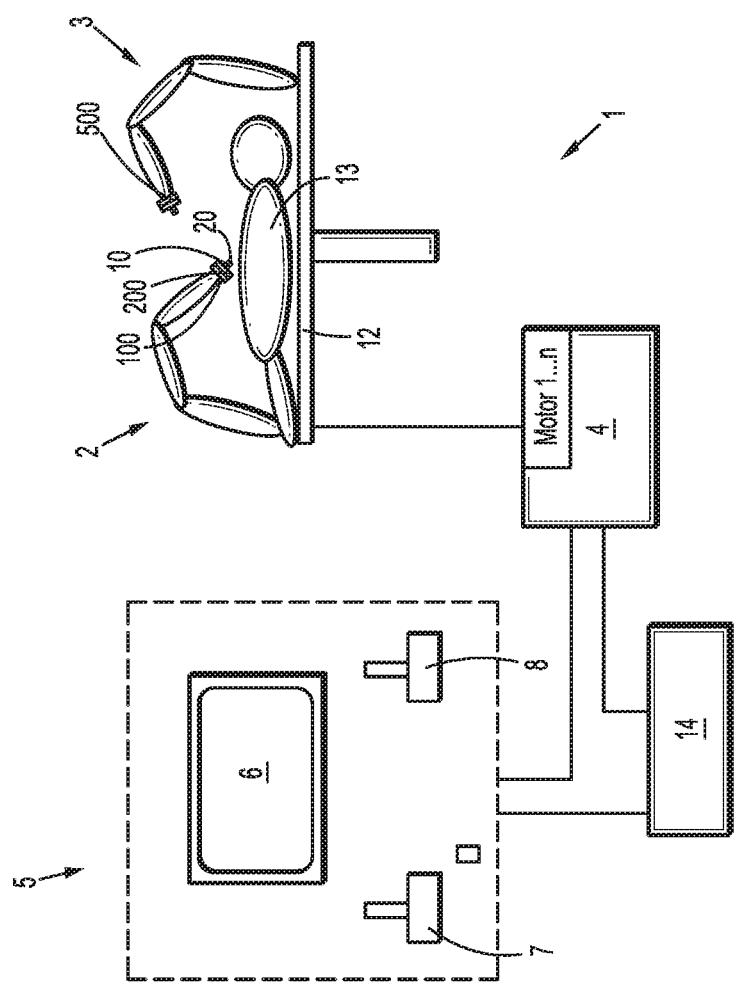
FIG. 1A is a schematic illustration of a medical work station and operating console in accordance with the present disclosure.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument control unit 100 or a mounting structure 500. Instrument control unit 100 may be attached, for example, to a surgical instrument 10 having an instrument drive assembly 200, and supporting an end effector 20 having jaw members. Mounting structure 500 may be configured to slidingly accept, for example, a cannula assembly 600, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units 100 (and thus the surgical instruments 10), and mounting structure 500 (and thus the cannula assembly 600) execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of surgical instrument 10. Medical work station 1 may also include more than two robot arms 2, 3, the additional robot arms likewise being connected to control device 4 and being telemanipulatable by means of operating console 5. An instrument control unit, a surgical instrument, a mounting structure and/or a cannula assembly may also be attached or coupled to the additional robot arms. Medical work station 1 may include a database 14, in particular coupled to with control device 4, in which are stored for example pre-operative data from patient 13 and/or anatomical atlases.

Reference may be made to U.S. Pat. No. 8,828,023, entitled "Medical Workstation," the entire content of which is incorporated herein by reference, for a detailed discussion of the construction and operation of medical work station 1.

Control device 4 may control a plurality of motors (e.g., "M1"-"M6"). Motors may be part of instrument control unit 100 and/or disposed externally of instrument control unit 100. Motors "M" (e.g., motors "M" being located externally of instrument control unit 100) may be configured to rotate a crown gear "CG" (FIG. 1B), or the like, that is keyed to or non-rotatably supported on a rotatable shaft of at least some of motors "M." In use, as motors "M" are driven, the rotation of crown gear(s) "CG" effects operation and/or movement of instrument drive assembly 200 of surgical instrument 10, as discussed below. It is further envisioned that at least one motor "M" receives signals wirelessly (e.g., from control device 4). It is contemplated that control device 4 coordinates the activation of the various motors (Motor 1 . . . n) to coordinate an operation and/or movement of surgical instrument 10 and/or cannula assembly 600. It is envisioned that each motor corresponds to a separate degree of freedom of surgical instrument 10 engaged with instrument control unit 100. It is further envisioned that more than one motor, including every motor (Motor 1 . . . n), is used for each degree of freedom. Reference may be made to commonly owned International Patent Publication No. WO 2015/088647, filed on Oct. 20, 2014, entitled "Wrist and Jaw Assemblies for Robotic Surgical Systems," the entire content of which is incorporated herein by reference, for a detailed discussion of illustrative examples of the construction and operation of end effectors 20 for use with instrument control unit 100.

Figure 2:
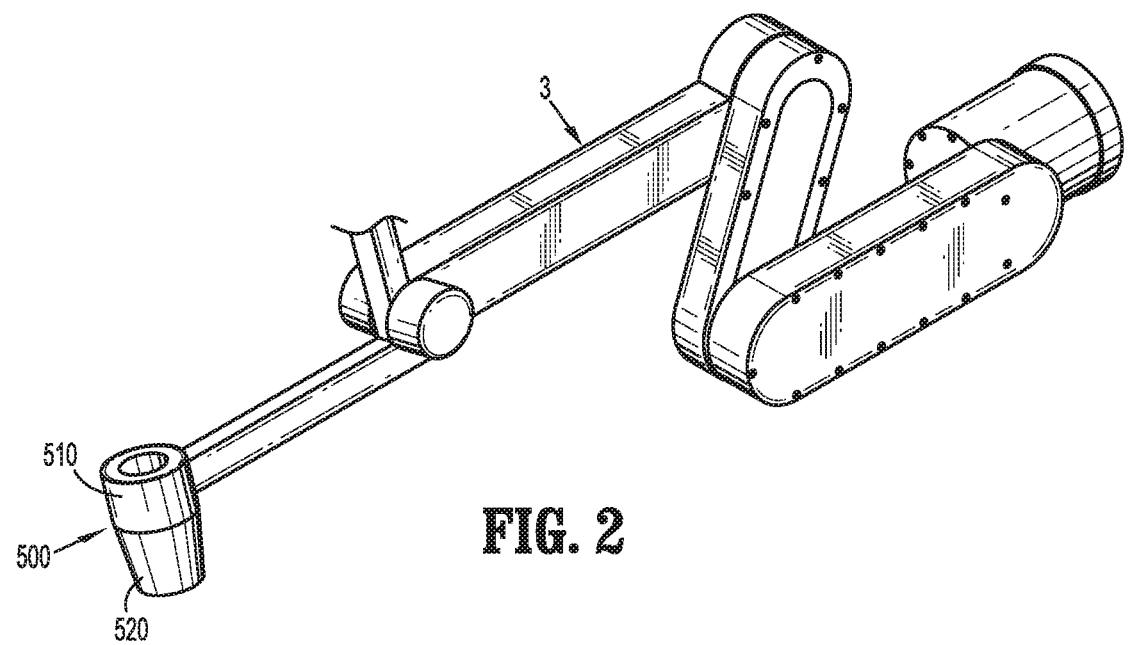
FIG. 2 is a perspective view of an arm of the medical work station of FIGS. 1A and 1B including a mounting structure thereon.
Figure 3:
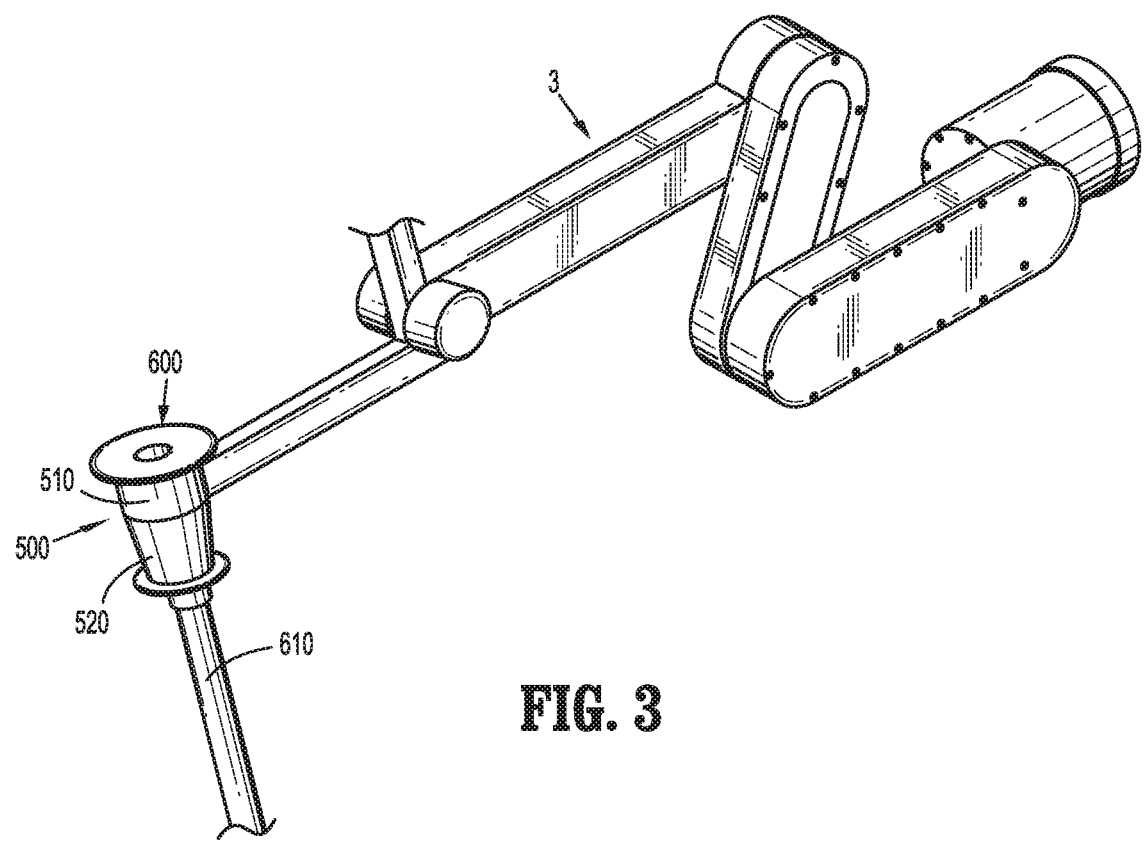
FIG. 3 is a perspective view of the arm and mounting structure of FIG. 2 including a cannula assembly extending through the mounting structure.

Turning now to FIGS. 2-3, robot arm 3 is shown supporting mounting structure 500. It is envisioned that mounting structure 500 is removably or fixedly coupled to robot arm 3. It is further envisioned that a portion (e.g., a proximal housing 510) of mounting structure 500 is rotatable with respect to another portion (e.g., a distal housing 520) of mounting structure 500, such that at least a portion of mounting structure 500 is rotatable with respect to robot arm 3. As discussed in further detail below, mounting structure 500 is configured to accept cannula assembly 600 at least partially therein. For example, at least a portion of cannula assembly 600 may be inserted through a channel 530 extending through mounting structure 500 in the general direction of arrow "A" in FIG. 3, from a distal direction toward a proximal direction.

Additionally, a conventional access port is usable with cannula assembly 600 (e.g., in embodiments using medical work station 10 in FIG. 1A). In such uses, alignment between the robotic arm 3 and the access port is maintained, thereby removing the need to simultaneously align the surgical instrument 10 with the robot arm 3 and align the surgical instrument 10 with the access port.

Figure 4:
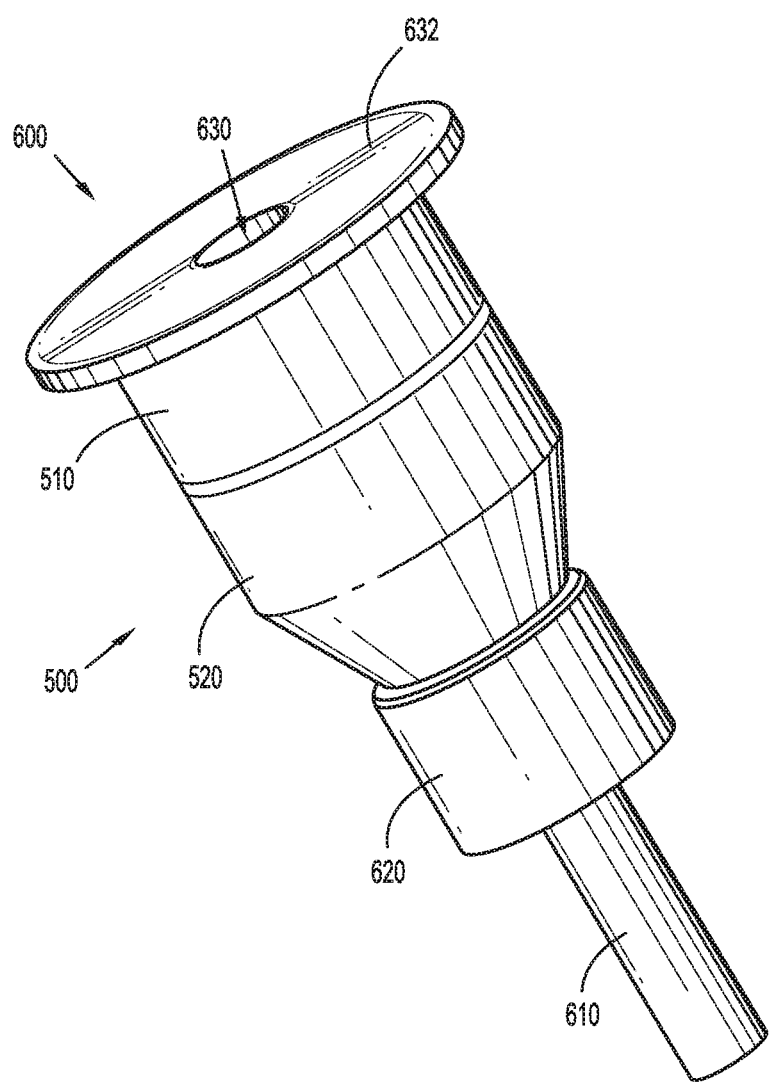
FIG. 4 is a perspective view of the mounting structure and cannula assembly of FIG. 3.
Figure 5:
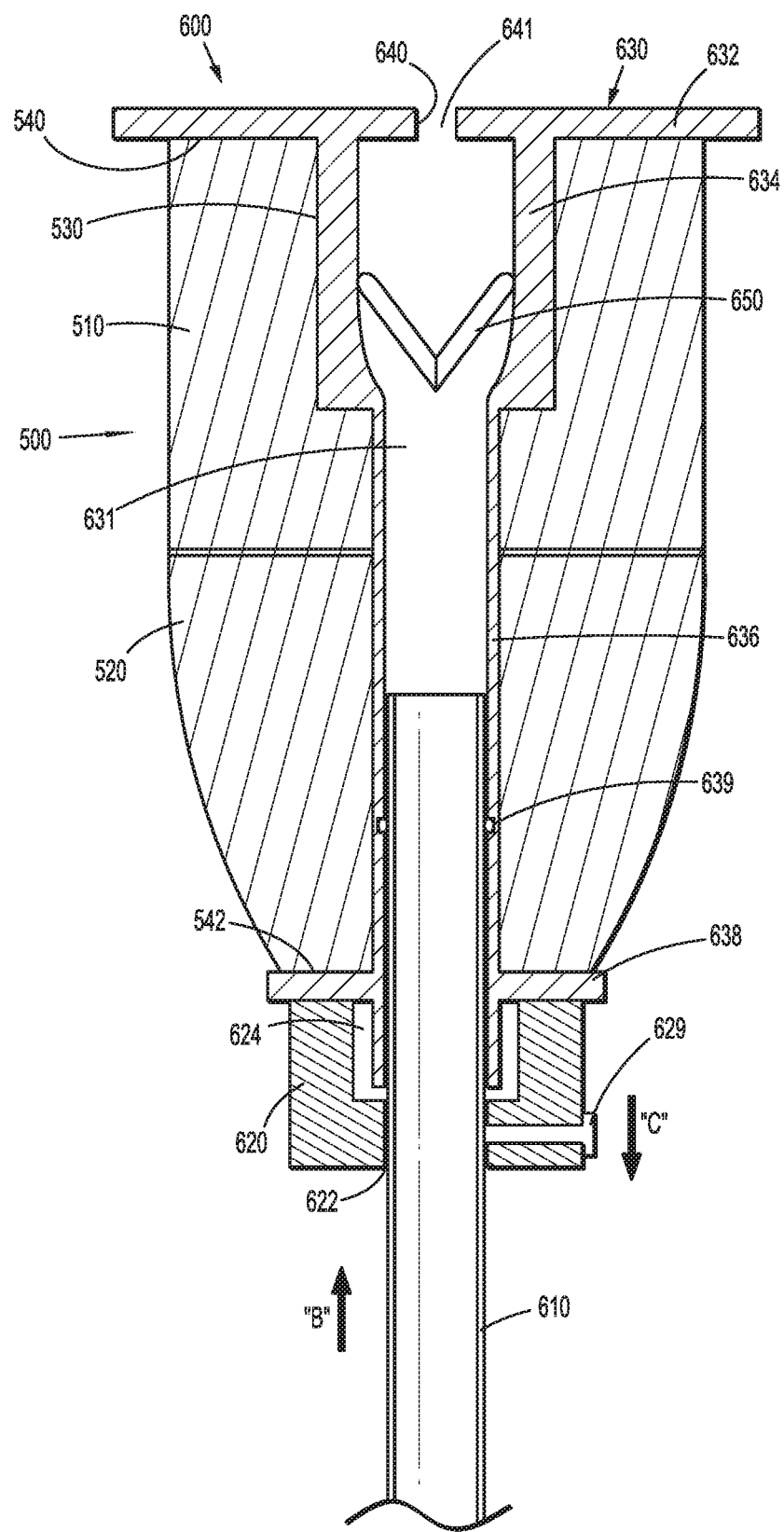
FIG. 5 is a cross-sectional view of the mounting structure and cannula assembly of FIGS. 3 and 4.

Referring to FIGS. 4 and 5, cannula assembly 600 is shown extending through mounting structure 500. Cannula assembly 600 includes a cannula or trocar 610, an attachment member 620, a barrier 630, a first seal 640, and a second seal 650. Generally, cannula assembly 600 is configured to provide a passageway for a surgical instrument (e.g., surgical instrument 10) to be inserted through an incision in a patient's skin and adjacent target tissue. Additionally, as discussed in further detail below, cannula assembly 600 is configured to minimize or prevent gasses and/or fluids from exiting the patient proximally through cannula assembly 600, for example.

Cannula 610 is an elongated, hollow tube that is configured to allow an elongated portion and an end effector of a surgical instrument to pass therethrough and access target tissue within a patient, for example. Cannula 610 is sized and dimensioned for insertion within a channel 530 of mounting structure 500. More particularly, cannula 610 is configured to be inserted into channel 530 of mounting structure 500 in a distal-to-proximal direction (in the general direction of arrow "B" in FIG. 5), and cannula 610 may be removed from channel 530 in a proximal-to-distal direction (in the general direction of arrow "C" in FIG. 5). An outer diameter of cannula 610 and an inner diameter of barrier 630 (e.g., a distal cylindrical section 636) within channel 530 of mounting structure 500 may be similarly sized to enable a frictional engagement therebetween.

With continued reference to FIGS. 4 and 5, attachment member 620 is a ring-like, cylindrical tube including a longitudinal cavity 622 extending therethrough, and including a proximal recess 624 therein. As shown in FIG. 5, cannula 610 is sized and dimensioned to extend through longitudinal cavity 622 of attachment member 620. More particularly, the present disclosure envisions that cannula 610 is fixedly attached to attachment member 620, is frictionally engaged with attachment member 620, or is mechanically fastened or able to be fastened to attachment member 620. For instance, it is envisioned that attachment member 620 engages cannula 610 with mechanical structure such as a set screw 629 (as shown in FIG. 5), break-away snaps (not explicitly shown), ribs designed to fracture in response to a predetermined amount of force (not explicitly shown), a bayonet-type connection, etc. It is further envisioned that the engagement between attachment member 620 and cannula 610 allows cannula 610 to be removed from mounting structure 500 in a distal-to-proximal direction (in the general direction of arrow "B" in FIG. 5), such that cannula 610 can be removed from mounting structure 500 in either a distal-to-proximal direction or a proximal-to-distal direction. For instance, attachment member 620 may be removed from cannula 610, e.g., by loosening set screw 629, and cannula 610 may be forced proximally through a lumen 631 within barrier 630 and out of engagement with the patient 13.

Additionally, cannula assembly 600 may completely lack attachment member 620. In such embodiments, cannula 610 directly engages barrier 630 (e.g., a threaded connection therebetween), and a distal-to-proximal disengagement of cannula 610 with respect to barrier 630 may not be feasible.

With particular reference to FIG. 5, barrier 630 is shown. Barrier 630 may be made from poly-ethyene, nylon, polypropylene, Acetal, ABS, poly-carbonate, Poly-sulphone, PEEK, Radel, silicon, etc., and is configured to minimize or prevent contamination of mounting structure 500, instrument control unit 100, surgical instrument 10, etc. from bodily fluids that were in contact with cannula 610 during use, for example. Barrier 630 defines lumen 631, and includes a proximal ring 632, a proximal cylindrical section 634, a distal cylindrical section 636, and a distal ring 638. Proximal ring 632 is positioned adjacent to or in contact with a proximal face 540 of mounting structure 500. Proximal cylindrical section 634 extends distally from proximal ring 632 and is positioned within channel 530 of mounting structure 500 (e.g., within channel 530 of proximal housing 510). Distal cylindrical section 636 extends distally from proximal cylindrical section 634, extends through channel 530, and extends distally of a distal face 542 of mounting structure 500. Distal ring 638 is positioned adjacent to or in contact with distal face 542 of mounting structure 500, and radially surrounds a portion of distal cylindrical section 636. Distal ring 638 may be affixed to distal cylindrical section 636 or may be longitudinally movable with respect to distal cylindrical section 636. For example, distal ring 638 may be removable from the remainder of barrier 630. As shown in FIG. 5, at least one O-ring 639 may be included (e.g., integrated into barrier 630) to help ensure a secure engagement with little to no "play" between cannula 610 and barrier 630.

Further, a quick-connect mechanism may be utilized to enable or facilitate mechanical engagement between cannula 610, attachment member 620 and/or barrier 630. For example, attachment member 620 may include threads on proximal recess 624 which engage corresponding threads on distal cylindrical section 636 (e.g., the portion of distal cylindrical section 636 that extends distally of distal ring 638). A bayonet-, twist-, or snap-type connection may also be utilized between attachment member 620 and barrier 630.

With reference to FIG. 5, first seal 640 is disposed within proximal ring 632 of barrier 630. First seal 640, e.g., a septum seal or an instrument seal, is configured as a hole or opening, for instance, radially centered on proximal ring 632. First seal 640 is configured to maintain a fluid- and/or air-tight seal between areas located distally of first seal 640 and areas located proximally of first seal 640 while a surgical instrument (e.g., surgical instrument 10) extends through a hole 641 first seal 640 (e.g., to prevent or minimize the amount of insufflation gasses capable of escaping the patient during a surgical procedure). It is envisioned that first seal 640 is formed from the same material as barrier 630 (e.g., material directly adjacent hole 641 is made from the same material as barrier 630), or that first seal 640 includes a different material (e.g. disposable plastic or a reusable material) that is attached to barrier 630.

With continued reference to FIG. 5, second seal 650 is shown disposed within proximal housing 510 of mounting structure 500. Second seal 650, e.g., a duckbill seal, is radially centered within proximal cylindrical section 634 of barrier 630. Second seal 650 is configured to maintain a fluid- and/or air-tight seal between areas located distally of first seal 640 and areas located proximally of first seal 640 without the presence of a surgical instrument inserted therethrough (e.g., to prevent or minimize the amount of insufflation gasses capable of escaping the patient prior to a surgical instrument is inserted through cannula 610 and/or after a surgical instrument is removed from cannula 610). It is envisioned that second seal 650 is made from the same material as barrier 630 or from a different material.

The present disclosure also includes methods of engaging cannula 610 with mounting structure 500 of robot arm 3. For example, methods include inserting a portion of cannula 610 within mounting structure 500 in a distal-to-proximal direction. Methods also include removing the cannula 610 from engagement with mounting structure 500 in a proximal-to-distal direction and/or a distal-to-proximal direction, inserting barrier 630 at least partially within channel 530 of mounting structure 500, engaging attachment member 620 with barrier 630, and removably securing attachment member 620 to cannula 610, for instance.

The use of cannula assembly 600 and mounting structure 500 may also enable nurses or assistants to insert the surgical instrument(s) 10 (as alignment is facilitated using mounting structure 500), while the surgeon focuses on the precise location of the end effector 20 of the surgical instrument 10 with respect to target tissue. This process may lead to faster instrument insertion, and may help prevent inadvertently contacting adjacent tissue with the end effector 20.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical cannula assembly for use with a mounting structure of a robotic arm, the surgical cannula assembly comprising:
   a cannula configured for reception of a surgical instrument at least partially therethrough;
   an attachment mechanism configured to releasably engage the cannula; and
   a barrier configured to extend through a channel of the mounting structure, the barrier including a proximal ring for positioning adjacent a proximal face of the mounting structure, a distal ring for positioning adjacent a distal face of the mounting structure, and a cylindrical section defining a lumen therein and extending between the proximal ring and the distal ring, the cannula configured for insertion within the lumen in a distal-to-proximal direction; wherein the cannula is configured for removal from the lumen in a distal-to-proximal direction.

2. The surgical cannula assembly according to claim 1, wherein the barrier is configured to provide a sterile barrier between the cannula and the mounting structure during use.

3. The surgical cannula assembly according to claim 1, further comprising a first seal disposed within the lumen of the barrier and being configured to provide an air-tight seal about a surgical instrument that is inserted through a hole defined by the first seal.

4. The surgical cannula assembly according to claim 3, further comprising a second seal disposed within the lumen of the barrier and being configured to provide an air-tight seal within the lumen of the barrier in the absence of a surgical instrument within the lumen of the barrier.

5. The surgical cannula assembly according to claim 4, wherein the first seal and the second seal are made from the same material as the barrier.

6. The surgical cannula assembly according to claim 1, wherein the cannula is configured for removal from the lumen of the barrier in a proximal-to-distal direction.

7. A method of engaging a cannula with a mounting structure of a robotic arm, comprising:

inserting a portion of a cannula within a channel of the mounting structure in a distal-to-proximal direction, the cannula providing a path through which a surgical instrument can be inserted in a proximal-to-distal direction at least partially therethrough to access a patient; inserting a barrier at least partially within the channel of the mounting structure; engaging an attachment member with the barrier, and removably securing the attachment member to the cannula; removing the cannula from engagement with the mounting structure in a distal-to-proximal direction by loosening the engagement between the attachment member with the cannula.

\* \* \* \* \*